(12) United States Patent
Mosk et al.

(10) Patent No.: US 6,882,884 B1
(45) Date of Patent: Apr. 19, 2005

(54) PROCESS FOR THE STIMULATION OF PRODUCTION OF EXTRACELLULAR DERMAL PROTEINS IN HUMAN TISSUE

(75) Inventors: Michael D. Mosk, Oswego, IL (US); Michael M. Breen, River Forest, IL (US)

(73) Assignee: Soundskin, L.L.C., Oswego, IL (US)

( * ) Notice: Subject to any disclaimer, the term of this patent is extended or adjusted under 35 U.S.C. 154(b) by 43 days.

(21) Appl. No.: 09/977,051

(22) Filed: Oct. 12, 2001

Related U.S. Application Data

(60) Provisional application No. 60/240,572, filed on Oct. 13, 2000, and provisional application No. 60/274,814, filed on Mar. 9, 2001.

(51) Int. Cl.$^7$ ................................................ A61N 1/08
(52) U.S. Cl. ....................................................... 607/50
(58) Field of Search ....................... 604/20–22; 601/2; 607/3, 50

(56) References Cited

U.S. PATENT DOCUMENTS

| | | | |
|---|---|---|---|
| 4,368,410 A | 1/1983 | Hance et al. ................ 318/116 |
| 4,580,570 A | 4/1986 | Sarrell et al. ............... 128/421 |
| 4,786,277 A | 11/1988 | Powers et al. ................ 604/20 |
| 4,791,915 A | 12/1988 | Barsotti et al. ............ 128/24 A |
| 4,895,154 A | 1/1990 | Bartelt et al. ............... 128/421 |
| 5,024,236 A | 6/1991 | Shapiro ....................... 128/735 |
| 5,445,611 A | 8/1995 | Eppstein et al. ............... 604/49 |
| 5,512,475 A | 4/1996 | Naughton et al. .... 435/240.243 |
| 5,538,503 A * | 7/1996 | Henley .......................... 604/20 |
| 5,582,586 A * | 12/1996 | Tachibana et al. ............. 604/20 |
| 5,617,851 A | 4/1997 | Lipkovker ................... 128/632 |
| 5,665,141 A | 9/1997 | Vago ............................. 95/30 |
| 5,667,487 A | 9/1997 | Henley ........................ 604/20 |
| 5,776,170 A | 7/1998 | MacDonald et al. .......... 607/46 |
| 5,947,921 A * | 9/1999 | Johnson et al. ................ 604/22 |
| 5,948,011 A | 9/1999 | Knowlton .................... 607/101 |
| 5,974,342 A | 10/1999 | Petrofsky ..................... 607/50 |
| 5,989,245 A | 11/1999 | Prescott ........................ 606/14 |
| 6,030,374 A | 2/2000 | McDaniel .................... 604/506 |
| 6,041,253 A * | 3/2000 | Kost et al. ..................... 604/20 |
| 6,302,874 B1 * | 10/2001 | Zhang et al. | |

FOREIGN PATENT DOCUMENTS

| | | | |
|---|---|---|---|
| DE | 4229693 A1 | 9/1992 | ............ A61N/1/32 |
| GB | 2263406 A | 7/1993 | ........... A61H/23/00 |
| WO | WO 97/07734 | 3/1997 | ............. A61B/5/00 |
| WO | WO 98/00193 | 1/1998 | ........... A61M/31/00 |
| WO | WO 98/29134 | 7/1998 | ........... A61K/41/00 |
| WO | WO 99/44637 | 9/1999 | ........... A61K/41/00 |

OTHER PUBLICATIONS

"In Vitro Effects of Therapeutic Ultrasound on Cell Proliferation, Protein Synthesis, and Cytokine Production by Human Fibroblast, Osteoblasts and Monocytes" J. Oral Maxillofac Surg Apr. 1999; 57(4):407–19.*

"The Healing of Superficial Wounds is Stimulated by External Electrical Current" Alvarez et al J. Invest Dermatol Aug. 1983; 81(2):144–8.*

* cited by examiner

*Primary Examiner*—Mark Bockelman
(74) *Attorney, Agent, or Firm*—Fellers, Snider, Blankenship, Bailey & Tippens, P.C.

(57) ABSTRACT

A process for the stimulation of production of extracellular dermal matrix proteins in human tissue through the simultaneous delivery of ultrasound and electrical energy thereto. In another aspect, a wound is purposefully created in the dermal layer of the skin to stimulate natural healing processes to be followed by delivery of ultrasound and electrical energy to further advance the production of extracellular dermal proteins.

25 Claims, No Drawings

PROCESS FOR THE STIMULATION OF PRODUCTION OF EXTRACELLULAR DERMAL PROTEINS IN HUMAN TISSUE

CROSS REFERENCE TO RELATED APPLICATION

This application claims priority from copending provisional application Ser. No. 60/240,572, filed Oct. 13, 2000, and copending provisional application Ser. No. 60/274,814, filed Mar. 9, 2001.

BACKGROUND OF THE INVENTION

1. Field of the Invention

This invention relates to a process for the stimulation of production of extracellular dermal matrix proteins in human tissue through the simultaneous delivery of ultrasound and electrical energy thereto. In another aspect, a wound is purposefully created in the dermal layer of the skin to stimulate natural healing processes to be followed by delivery of ultrasound and electrical energy to further advance the production of extracellular dermal proteins (biological protein polymers).

2. Background

Electrical stimulation (e-stim) has been used for years in the healing arts and has been applied in many different waveforms and configurations. As with many other modalities and drugs in medicine, its validity is often overshadowed by exaggerated claims. Electrical stimulation has historically fallen into this category, but has always maintained a place in therapy because of its benefits. Transcutaneous electrical nerve stimulation for pain relief and low intensity direct current for bone mending of non-union fractures drew positive attention to e-stim in recent years. Wound healing in general has always been an excellent vehicle for e-stim primarily with decubitus ulcers. Later studies have indicated that e-stim has been widely accepted and provides numerous benefits such as improved blood flow and bacterial growth inhibition. The question involved in the use of e-stim is that of what waveform should be utilized in the treatment of human tissue since in keeping with the Arndt-Schultz Principle, too little stimuli does nothing, the proper amount will evoke the correct response, and too much can have a destructive effect. A number of commercially manufactured portable electrode systems are available to the public for e-stim applications. Typcially, these systems contain electrodes in pads composed of natural or synthetic gums and gels as the materials directly in contact with the skin. The various electrical circuits are attached to the pad and the electrical energy is transmitted first to the pad. Examples of e-stim electrode systems include those described in U.S. Pat. Nos. 5,974,342; 5,776,170; 4,895,154; 4,786,277 and 4,580,570, which patents are incorporated herein by reference.

The use of ultrasound in physical therapy has been widely practiced with a variety of devices which are intended for transmitting either continuous or pulsed ultrasound energy to the body of a patient for the treatment of various maladies. One such system is that disclosed in Barsotti et al, U.S. Pat. No. 4,791,915, said patent also being incorporated by reference herein. However, with standard external ultrasound there are two basic problems. The first is the power displayed on the meter is never the power delivered in tissue. The second problem is beam uniformity. In the absence of a collimated beam pattern the beam pattern converges and creates a hot spot in the middle.

Thus there is presented a need with the application of ultrasound and e-stim for systems which will overcome the art recognized shortcomings of the currently available systems.

In addition, in attempting to maintain a youthful appearance, it is necessary to stimulate the production of collagen III fibers and elastin to achieve an optimal clinical end result of tissue response that is more consistent with normal healthy tissue. Also, in the normal aging process of the skin which tends to convert collagen III fibers to collagen I fibers through cross-linkage and dimer production, the lack of collagen III fibers and elastin results in the inability of the skin to withstand detrimental external irritants over time and skin that is less resilient.

Thus there is presented a need for a process which will effect the production of collagen III fibers and elastin in human tissue.

It is thus an object of the present invention to provide a process for the effective treatment of human tissue which will effect the production of extracellular dermal proteins in human tissue.

Another object of this invention is to provide a process for the treatment of human tissue to as to stimulate the production of the protein collagen.

A further object of this invention is to provide a process whereby there is produced resilient collagen and elastin in human tissue.

SUMMARY OF THE INVENTION

In accordance with one embodiment of the present invention, it has been discovered that through the simultaneous delivery of ultrasound and electrical energy to human tissue there is achieved a safe, accurate and reproducible process for the stimulation of the production of a biological polymer consisting of amino acids commonly referred to as the protein collagen, as well as elastin and reticulin.

Such a process is based upon the discovery that with the simultaneous delivery of ultrasound and electrical energy to the tissue, through the use of a low energy micro-amperage there is stimulated the production of the polypeptide collagen and the ultrasound creates a mechanical pressure gradient on the cells that produces specific resilient collagen and elastin.

Thus by the present invention there is provided a process for the selective stimulation of biological protein polymers in human tissue which comprises simultaneously delivering of ultrasound and electrical energy to a selected locus of said tissue.

Relatedly, there is further provided a means of stimulating the natural healing process and subsequent production of collagen to be followed by delivery of ultrasound and electrical energy as aforedescribed to further advance the production of biological protein polymers. In connection with this embodiment, a wound is created in the dermal layer of skin in a manner that does not remove or disrupt in any way the stratum corneum or epidermis. Thereafter, within the first 24 hours, low intensity ultrasound and e-stim is used to accelerate and enhance the healing process and stimulate the production of new collagen fibers.

A better understanding of the present invention, its several aspects, and its objects and advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENT

Collagen is a complex family of triple helical proteins. Collagens are fibrous proteins that provide much of the tensile strength of the skin, tendons, and bone. There are nineteen known collagen protein polymers and the dermal matrix of epithelial tissue has a predominance of Collagen polymers of types I and III. Collagen I and III are stabilized by intermolecular covalent cross-links: the initial divalent cross-links dehydrohydroxylysinonorleucine (D-HLNL) and hydroxylysino-keto-norleucine (HLKNL) are converted to stable trivalent cross-links, histidino-hydroxylysinonorleucine (HHL) and hydroxylyslpyridino-line (pyrid) respectively, as the tissue matures. The relative proportion of initial divalent cross-links to the mature, trivalent cross-links provides an assessment of the maturity of the collagen fibrils and collagen fibrillar bundles. Collagen II is predominantly found in cartilage and the vitreous humor of the eye, while the minor collagen, fibrillar proteins, V and XI, are found in joint and bone matrices. All these collagen polymers share the same characteristics: a large triple-helical domain of approximately 1000 amino acid residues flanked by N-and C terminal globular extensions. The formation of the triple helix depends on the full hydroxylation of the proline in the third position of the chain triplets and the glycosylation and intermolecular cross-links, which depend on the hydroxylation of the target lysyl residues. After the nucleation and propagation of the helix, the molecule is stabilized by the formation of inter-chain disulfide bonds involving cysteine residues within the C-propeptides. When these propeptides are secreted into the extracellular space, the resulting molecule corresponds to a soluble precursor known as procollagen. This procollagen polypeptide entity rapidly undergoes alterations ensured by specific metalloproteases that release the N-and C terminal extensions. This is the process that is necessary for the formation and assembly of striated bundles of collagen fibrils. The balance of the dermal matrix synthesis and degradation of these collagen polymers are important for tissue integrity because tissue remodeling occurs continuously. Degradation depends on the activity of proteinases or proteases, secreted from connective-tissue cells, and these include the metalloproteases (MMPs) and acid cathepsins. There have been nine members of the MMP family identified in human beings, two (2) of which, interstitial and neutrophil collagenases (MMP 1 and 8) are capable of cleaving fibrillar collagen; while gelatinases (MMP 2 and 9) degrade the resulting denatured peptides. Acid cathepsins depolymerise collagen fibers by cleaving near cross-link sites. The combined action of these enzymes is capable of degrading all components of the extracellular matrix. All these enzymes may be regulated by modulation of proenzyme production or activation, or by changing levels of endogenous inhibitors.

The remodeling of the extracellular matrix involves innumerable steps, including the recruitment, accumulation, and eventual apoptosis of the parenchymal cells (fibroblasts, mast cells, lymphocytes) with their accompanying degranulation, involving the release of leucokinetic and cytokinetic factors and the production, organization, and the rearrangement of the extracellular protein matrix produced by these cells.

The present invention is based upon the discovery that through the use of a process which utilizes the simultaneous delivery of ultrasound and electrical energy to a selected locus on human tissue there is achieved a safe, accurate and reproducible process to stimulate the production of collagen, and particularly collagen III, as well as elastin and reticulin.

Both the electrical and ultrasound energy create unique types of harmonic resonance on the surface of cells being stimulated. Through the use of a low energy micro-amperage electrical stimulation there is effected the production of the polypeptide collagen while the ultrasound creates a mechanical pressure gradient on the cells that produces specific resilient collagen and elastin.

The process of this invention stimulates those genetically programmed cells, called fibroblasts, for collagen production. This stimulation also increases the production of the proteins elastin and reticulin. Effective stimulation mandates the following principles: 1) The Arndt-Schultz principle which states that any stimuli must be delivered in proper dosage or intensity to evoke the proper tissue response. Too little stimuli will have no stimulatory effect and too high of an intensity stimuli will have a destructive effect. 2) Stimulation must be delivered to the desired location within the tissue without damage to the tissue and reduction or degradation of the stimuli signal itself, which would render the stimuli ineffective.

The electrical energy utilized in the process of the present invention meets the above criteria. The waveform used is a twin-peaked, unidirectional, capacitor-discharged, high potential waveform with low energy. The voltage or potential allows the energy to penetrate the normally resistant stratum corneum of the epidermis while the low energy limits the stimulation current to safe effective levels of stimulation. Voltage is adjustable from 1–500 volts. Treatment is given at a voltage that renders minimal sensory response from the patient, i.e., a tingling effect, usually between 20–150 volts. This current is nominally about 100 microamps and is of short duration for stimulating a physiologic response on a cellular level. The complex capacitive discharge waveform consists of the mathematical sum of many waveforms. It consists of low frequencies, represented by the time between pulse pairs (double pulses), to very high frequencies represented by the extremely fast rise time of the individual pulses—nominally about 150 nanoseconds. This wide spectral content of the waveform provides both low frequency "stimulatory" effects and high frequency multi-facilitory effects.

Through the practice of the present invention there is addressed another important factor of stimulation which is the ability of cells to accommodate to a particular stimuli. Accommodation occurs when the stimuli becomes familiar to the cells being stimulated and eventually these cells fail to respond. The present process uses a sweeping or modulating frequency. This is an automatic adjustment of pulse frequency from about 5 pulses per second to about 105 pulses per second, then back to about 5 pulses per second and so forth. This rotation of sort is enough of a variation to the cells to prevent them from accommodating to a constant stimulation by recurrent stimuli.

The electrical energy, as delivered per the present invention, will stimulate primarily the production of collagen I fibers. Collagen I fibers are larger and less resilient than the smaller collagen III fibers. Simply stimulating the production of collagen I fibers will offer a potentially thicker less pliable or elastic tissue when treating a wound. Therefore, it is necessary to stimulate the production of collagen III fibers and elastin to achieve an optimal critical end result of tissue response that is more consistent with normal healthy tissue. Through the normal aging process of skin collagen III fibers are converted to collagen I fibers through cross-linkage and dimer production. Thus the lack of collagen III fibers and elastin result in the inability of the skin to withstand detrimental external irritants over time and skin that is less resilient, which in turn results in an aged appearance. Such difficulties are overcome by the process of the present invention which stimulates the production of collagen III fibers and elastin so as to maintain a normal healthy tissue appearance.

The ultrasound energy propagates ultrasound waves into the tissue. Such waves are uniform, deep penetrating, consistent and create a pressure gradient across the cell membrane. This pressure gradient creates a stress on the cell surface. This force creates stress-generated voltages which are important to the production, alignment and maintenance of collagen fibers, especially the more elastic and resilient collagen III fibers and elastin. Therefore, it is important to simultaneously stimulate with electrical energy and ultrasound to achieve the optimal tissue matrix consisting of the fibrous polypeptide components: collagen, elastin and reticulin.

Ultrasound, as with the electrical energy, must be delivered in the appropriate dosages and to the proper location within the tissue. In the practice of the present invention there is preferably utilized a 2.2 Megahertz frequency. The ultrasound frequency determines the basic depth of penetration into the tissue. In carrying out the process of this invention a frequency in the range of about 1 to about 4 Megahertz can be employed.

Ultrasound energy should be in the range of about 0.1 watts per squared centimeter to about 0.5 watts. Presently preferred is a setting of about 0.3 watts per centimeter squared. Higher watts per centimeter squared are used when heat is desired. Eventually watts up to 2–3 watts per centimeter squared, along with extended time on tissue, can result in tissue disruption/destruction.

In carrying out the process of this invention, it is extremely important to maintain the optimum energy level since too little ultrasound energy is not an effective stimulus and too much ultrasound energy will destroy tissue at the cellular level. To insure that the exact or correct power is being delivered regardless of varying tissue acoustic impedances, which can dramatically alter the power transferred to tissue, there is employed in the practice of the process of this invention a servo-loop feedback system to monitor the power actually being delivered to the tissue. The servo-loop technology actually responds to tissue impedances and instantaneously compensates to maintain the exact dosage desired for carrying out the delivery of ultrasound to the selected tissue locus.

In the practice of the process of this invention there is employed a soundhead for the ultrasound that delivers a totally collimated beam pattern so as to achieve an even distribution of ultrasound energy. An uneven distribution of ultrasound energy can cause "hot spots" which may destroy cells or "cold spots" where no energy is delivered and consequently no stimuli.

It is important in the practice of the process of this invention that perfectly gated blocks of ultrasound energy be provided so as to insure accurate and reproducible results. The ultrasound energy may be delivered in either a pulsed or in a continuous manner. The pulsed format is preferred for delivery due to its off periods which helps prevent heat build up and damage to the cells being stimulated. This pulsed ultrasound aspect of the method uses a "sweeping" pulse width for the delivery of the pulses, in synchronization with the electrical stimulation component. The ultrasound pulses are modulated from about a 5% duty cycle to a 50% duty cycle and back to 5% and so forth. A 5% duty cycle means the ultrasound energy is on for 5% of the time and off for 95% of the time. Similarly a 10% duty cycle is on for 10% and off for 90% and so on. Thus there can be employed modulated ultrasound pulses in the range of from about 5% to about 50% duty cycle. In employing such a range of pulsed ultrasound there is prevented accommodation that is similar to that of the electrical component of the present process.

A further benefit of using a simultaneous delivery of ultrasound and electrical energy to stimulate various fibrous dermal components like collagen, is the ability of these combined modalities to increase blood flow the area being treated. Increased blood flow improves oxygenation, micro/macro nutrient delivery to the tissue and thereby facilitates the removal of enzymatic free radicals and byproducts. Such factors are valuable whether a wound is being stimulated to heal or normal tissue is being stimulated to improve the texture of the skin.

It can thus be seen that simultaneous delivery of specific ultrasound and electric energy in accordance with the present invention will selectively stimulate the production of collagen, elastin and reticulin. When these energy sources are used simultaneously to stimulate, the resultant tissue matrix formation will be improved as compared to using either modality independently. The success of these energy forms can only be achieved when such are carried out under the specific parameters as disclosed herein and through the utilization of a system which has the ability to successfully deliver these parameters.

The inventive process may be practiced utilizing well known commercially available componentry set to deliver e-stim and ultrasound in the manner provided. It may be practiced utilizing two machines, each delivering one of the required components, or it may be practiced utilizing a single machine providing both e-stim and ultrasound.

While the above discussion has identified the necessary parameters for the simultaneous delivery of ultrasound and electrical energy, it will be appreciated that various changes beyond those described will no doubt occur to those skilled in the art and such changes are to be understood as forming a part of this invention in so far as they fall within the spirit and scope of the invention.

A basic concept that has been accepted for years is that the creation of a wound will stimulate the natural healing process and the subsequent production of collagen. The present invention further contemplates stimulating the natural healing process and subsequent production of collagen through purposeful wound creation in the dermal layer of the skin followed by delivery of ultrasound and electrical energy as aforedescribed to further advance the production of biological protein polymers.

In this regard, there is provided a process for the rejuvenation of skin by the stimulation of collagen that utilizes multiple steps over a time period and as an ongoing process for skin maintenacne, to wit:

Step 1 involves the creation of a wound in the dermal layer of the skin. This may be accomplished via ultrasound, laser, diathermy, microwave or any other modality that has the ability to penetrate through the skin to the dermal tissue without disrupting, damaging, exfoliating any of the stratum corneum or epidermal tissue. The intensity used by any of the above modalities is that which is sufficient to cause a mild wound, i.e., disruption/destruction of dermal cellular and extracellular elements, localized only in the dermis, to stimulate the body's natural wound healing process.

Step 2 is initiated once the wound has been created and the healing process has been activated. Within the first 24 hours following wound creation, low intensity ultrasound/ e-stim is used to accelerate and enhance the healing process and the production of new collagen fibers. Collagen I and III as well as elastin and reticulin are all stimulated and produced as part of this process. It has been clearly noted in the healing of other wounds, such as decubitus ulcers, that it is extremely important to keep the wound site supplied with oxygen, minerals, and other nutrients. Compromised supply of any of the above will delay or retard the healing process. Conversely, the increased presence of the above will greatly enhance the healing of a wound that was artificially created in healthy tissue. Application of ultrasound/e-stim increases local circulation, promotes lymphatic drainage which reduces edema, and prevents the formation of a thrombus, thus providing all the above stated factors needed in wound repair and helping to alleviate any potential complications, as a result of the wound created.

The creation of the wound in the dermal layer of the skin results in collagen being increased internally with no external, visible signs of damage. Steps 3 and 4 are ways to enhance further collagen stimulation working externally.

Step 3 utilizes the same blended, modulated ultrasound/e-stim parameters to enhance the delivery and penetration of topical cremes or gels that contain known collagen stimulating ingredients, as well as ingredients for pigment lightening, anti-oxidant treatment, etc. This process, commonly called phonophoresis, is accomplished without the removal or damage of any of the stratum corneum or epidermal tissue. The blended, modulated ultrasound/e-stim energies increase cellular permeability and aid in the migration of the topical into the tissue.

Step 4 involves the mechanical exfoliation of the stratum corneum. This step is accomplished at times separate and distinct from the ultrasound/e-stim phonophoresis treatments. This mechanical exfoliation may be accomplished with oxide crystals, diamond abrasive tools or any device that systematically removes upper layers of tissue. This external process is one more form of stimulating collagen, especially with microdermabrasion systems that use a vacuum system. The vacuum mechanism of a microdermabrasion procedure itself offers its own value in the stimulation of blood flow and collagen production. This exfoliation may be done numerous times over a period of time targeting mild wrinkles and reducing their appearance.

In the process thus described, the internal wound is created first. Ultrasound and e-stim are used to enhance the healing process. They must be used shortly after the wound is created and can be used at any time during the treatment regime. Ultrasound/e-stim to enhance the delivery of topical agents may also be used at any point during the treatment regime, except when mechanical exfoliation is done. When doing the exfoliation it is not necessary to use the ultrasound for the normally resistant stratum corneum is compromised and topicals will effectively penetrate without the assistance of ultrasound. This process is a basic logical skin rejuvenation program that does not exclude the use of other treatments. For example, specific wavelength lasers may be used to remove vascular lesions, numerous topicals may be used to treat various skin problems, dietary supplements may be used to enhance the overall health of the skin, etc.

While the invention has been described with a certain degree of particularity, it is understood that the invention is not limited to the embodiment(s) set for herein for purposes of exemplification, but is to be limited only by the scope of the any claim or claims issued thereon, including the fill range of equivalency to which each element thereof is entitled.

What is claimed is:

1. A process for the stimulation of production of extracellular dermal matrix proteins in human tissue which comprises simultaneously delivering to said tissue ultrasound and electrical energy in an amount sufficient for the stimulation of production of extracellular dermal matrix proteins in human tissue;

wherein a current of said electrical energy is about 100 microamps; and wherein said ultrasound is provided at a frequency in a range of about 1 to about 4 megahertz.

2. A process according to claim 1 wherein said electrical energy is a low energy micro-amperage sufficient to stimulate the production of polypeptide collagen and said ultrasound is such that a mechanical pressure gradient is created in the cells that produces specific resilient collagen and elastin.

3. A process according to claim 2 wherein the wave form of said electrical energy is composed of a twin-peaked, unidirectional, capacitors-discharged, high potent wave form with low energy.

4. A process according to claim 3 wherein there is employed a voltage in the range of from about 1 to about 500 volts.

5. A process in accordance with claim 4 wherein there is employed a voltage in the range of about 20–150 volts.

6. A process according to claim 2 wherein said ultrasound is delivered in a continuous manner.

7. A process according to claim 2 wherein said electrical energy is provided at a pulse frequency in the range of from about 5 pulses per second to about 105 pulses per second.

8. A process in accordance with claim 2 wherein the ultrasound in synchronization with the electrical energy is modulated from about a 5% duty cycle to a 50% duty cycle and back to a 5% duty cycle.

9. A process according to claim 2 wherein said ultrasound is provided at an energy in the range of about 0.1–0.5 watts per squared centimeter.

10. A process according to claim 9 wherein said ultrasound energy is 0.3 watts per squared centimeter.

11. A process according to claim 2 wherein said ultrasound is pulsed.

12. A process for the stimulation of the natural healing processes in human skin tissue which comprises creating a wound in the dermal layer of said skin tissue and thereafter simultaneously delivering to said skin tissue ultrasound and electrical energy in an amount sufficient to stimulate natural healing processes in said skin tissue;

wherein a current of said electrical energy is about 100 microamps; and wherein said ultrasound is provided at a frequency in a range of about 1 to about 4 megahertz.

13. A process according to claim 12 wherein said wound is created in the dermal layer of skin with the avoidance of removal or disruption of the stratum corneum or epidermis.

14. A process according to claim 12 wherein the simultaneous delivery of said ultrasound and electrical energy is within 24 hours of the creation of said wound in the dermal layer of said skin tissue.

15. A process according to claim 12 wherein said ultrasound is provided at an energy in the range of about 0.1–0.5 watts per squared centimeter.

16. A process according to claim 15 wherein of said ultrasound energy is about 0.3 watts per squared centimeter.

17. A process according to claim 12 wherein said electrical energy is provided at pulse frequency in the range of from about 5 pulses per second to about 105 pulses per second.

18. A process according to claim 12 wherein said electrical energy is a low energy micro-amperage sufficient to stimulate the production of polypeptide collagen and said ultrasound is such that a mechanical pressure gradient is created in the cells that produces specific resilient collagen and elastin.

19. A process according to claim 12 wherein said ultrasound is pulsed.

20. A process according to claim 12 wherein said ultrasound is delivered in a continuous manner.

21. A process in accordance with claim 12 wherein the ultrasound in synchronization with the electrical energy is modulated from about a 5% duty cycle to a 50% duty cycle and back to a 5% duty cycle.

22. A process in accordance with claim 12 wherein said wound is accomplished by any modality having the ability to penetrate the skin to the dermal tissue without disruption, damaging or exfoliating any of the stratum corneum or epidermal tissue.

23. A process in accordance with claim 12 wherein the skin tissue is subjected to phonophoresis whereby a subsequent blended, modulated ultrasound and electrical energy is employed to enhance the delivery and penetration of topical creams or gels that contain collagen stimulating ingredients.

24. A process in accordance with claim 23 wherein following phonophoresis the stratum corneum of the skin is subjected to mechanical exfoliation.

25. A process in accordance with claim 24 wherein said mechanical exfoliation is carried out so as to systematically remove upper layers of tissue.

\* \* \* \* \*